United States Patent [19]
Kline

[11] Patent Number: 5,376,094
[45] Date of Patent: Dec. 27, 1994

[54] IMPROVED ACTUATING HANDLE WITH PULLEY SYSTEM FOR PROVIDING MECHANICAL ADVANTAGE TO A SURGICAL WORKING ELEMENT

[75] Inventor: Craig R. Kline, Spencer, Ind.

[73] Assignee: Boston Scientific Corporation, Watertown, Mass.

[21] Appl. No.: 109,609

[22] Filed: Aug. 19, 1993

[51] Int. Cl.⁵ .................... A61B 17/22; A61B 17/36
[52] U.S. Cl. .................................. 606/113; 606/110; 606/47; 606/127; 606/205
[58] Field of Search ............ 606/1, 32, 39, 40, 45-50, 606/110, 113, 114, 127, 128, 167, 179, 205-209

[56] References Cited

U.S. PATENT DOCUMENTS

| | | |
|---|---|---|
| 612,569 | 10/1898 | Moscrop. |
| 3,181,533 | 5/1962 | Heath. |
| 3,955,578 | 5/1976 | Chamness et al.. |
| 4,598,711 | 7/1986 | Deniega. |
| 4,733,671 | 3/1988 | Mehl. |
| 4,924,878 | 5/1990 | Nottke. |
| 4,971,067 | 11/1990 | Bolduc et al.. |
| 4,976,269 | 12/1990 | Mehl. |
| 5,084,054 | 1/1992 | Bencini et al.. |
| 5,111,828 | 5/1992 | Kornberg et al.. |
| 5,121,751 | 6/1992 | Panalletta. |
| 5,125,413 | 6/1992 | Baran. |
| 5,158,561 | 10/1992 | Rydell et al.. |
| 5,163,942 | 11/1992 | Rydell .................. 606/110 |
| 5,172,701 | 12/1992 | Leigh. |
| 5,300,078 | 4/1994 | Buelna .................. 606/113 |

FOREIGN PATENT DOCUMENTS

| | | |
|---|---|---|
| 0027704A2 | 4/1981 | European Pat. Off.. |
| 0152032A2 | 8/1985 | European Pat. Off.. |
| 0446020A1 | 9/1991 | European Pat. Off.. |
| 2628555A1 | 6/1976 | Germany. |
| 2628555C2 | 6/1976 | Germany. |
| 3632786A1 | 9/1986 | Germany. |
| 29470 | of 1913 | United Kingdom. |

OTHER PUBLICATIONS

Microvasive ® Boston Scientific Corporation, "Stone Retrieval" Catalogue, pp. 5-1 to 5-9, 5-31, and 5-35.

Primary Examiner—Stephen C. Pellegrino
Assistant Examiner—Glenn Dawson
Attorney, Agent, or Firm—Fish & Richardson

[57] ABSTRACT

A medical device has a body, an actuating member mounted to move relative to the body, a working element, and an elongated force-transmitting member capable of transmitting actuating force between the actuating member and the working element. The force-transmitting member includes a flexible cable portion, the force-transmitting member is attached, on one side of the cable portion, to the body and associated in a driving relationship on the opposite side of the cable portion with the working element. According to the invention the actuating member includes a pulley surface bodily movable therewith, the cable portion is trained about the pulley surface such that movement of the actuating member a given distance, relative to the body, causes the working element to move a substantially greater distance than the given distance. Another aspect of the invention is a medical snare with the above features.

24 Claims, 8 Drawing Sheets

IMPROVED ACTUATING HANDLE WITH PULLEY SYSTEM FOR PROVIDING MECHANICAL ADVANTAGE TO A SURGICAL WORKING ELEMENT

BACKGROUND OF THE INVENTION

There is a need for improved actuation for medical devices. One important example is the surgical snare handle. Snares are used to surgically remove polyps (pre-cancerous tissue growth in the colon and rectum), to remove esophageal carcinoma, and to perform nephrostomy. A snare device is inserted through a working channel of an endoscope fitted with a fiber optic camera, the output of which is attached to a video monitor.

In the case of a polyp, a doctor manipulates the endoscope in the tract of the patient until a polyp is located. The end of the snare in the form of a wire loop is extended and positioned around the polyp, and at the doctor's request, an assistant, typically a nurse, retracts the snare to cause the loop to retract and resect the polyp. An electrical current, such as r-f, is passed through the loop to cauterize the polyp and prevent bleeding.

The same technique is employed for other physical features to be excised or cut by a snare.

The snare is controlled by a snare handle. It is desirable that a snare handle have great fidelity so that whatever resistance is experienced by the snare is felt through the handle by the operator. If the operator cannot feel what is happening at the snare end, the polyp or other tissue might be severed before the cautery current has been applied, causing bleeding and other harmful consequences.

It is desirable that the snare be capable of extending fully and of retracting into the sheath a certain distance as a safety margin, for instance 0.75 inches. It is also desirable that the handle be constructed so that nurses with small hands can operate it.

Handles having good tactile feeling have long been available. These handles typically have one-to-one activation ratio in which the actuating element of the handle moves the same amount as the snare. Because the distance the snare must move is fairly large, these handles have been difficult to operate with one hand, especially for people with small hands. Attempts have been made to provide a handle which moves only a fraction of the distance of the snare travel. The presence of intervening parts, which may be subject to deformation under load, between the snare loop and the actuating member, however, has rendered the tactile sensitivity of these handles sub-optimal. Furthermore, these handles have also been complex, expensive to manufacture and have had other disadvantages.

SUMMARY OF THE INVENTION

In one aspect the invention comprises a medical device having a body, an actuating member mounted to move relative to the body, a working element, and an elongated force-transmitting member capable of transmitting actuating force between the actuating member and the working element. The force-transmitting member includes a flexible cable portion, the force-transmitting member is attached, on one side of the cable portion, to the body and is associated in a driving relationship on the opposite side of the cable portion with the working element. According to the invention the actuating member includes a pulley surface bodily movable therewith, the cable portion is trained about the pulley surface such that movement of the actuating member a given distance, relative to the body, causes the working element to move a substantially greater distance than the given distance.

Preferred embodiments of this aspect of the invention include one or more of the following features The pulley surface is a defined by a rigid formation rigidly joined to the actuating member, about which relative sliding motion of the cable portion occurs during actuation.

The flexible portion of the force transmitting member is substantially confined throughout its length to enable transmission of axial thrust on the working element.

The actuating member is mounted to translate relative to the body, thereby translating the pulley surface bodily relative to the body.

The body includes a rigid portion adjacent to the actuating member and an elongated flexible portion extending distally of the rigid portion through which distal portions of the force-transmitting member extend, preferably the medical device is in the form of a medical catheter.

The force-transmitting member is a flexible metal cable extending from the point of attachment to the body to the working element. Preferably, the cable comprises metal capable of high fidelity transmission of motion from the actuating member to the working element.

The actuating member has at least one loop engageable by a finger of an operator. Preferably, the body terminates in a central, relatively stationary, thumb loop and the actuating member defines two finger loops disposed on opposite sides of the thumb loop.

The actuating member includes a rigid guide tube extending to and slidably engaged with the body and the force-transmitting member extends through the guide tube an a sliding relationship.

The working element is either a snare, an angled snare loop, a grasper or a basket.

In another aspect, the invention comprises a medical snare device having a body, an actuating member mounted to move relative to the body, a snare, and a cable capable of transmitting actuating force between the actuating member and the snare, the cable is attached on one end to the body and is associated in a driving relationship on the opposite end with the snare. According to the invention the actuating member includes à pulley surface bodily movable therewith, the cable is trained about the pulley surface such that movement of the actuating member a given distance, relative to the body, causes the snare to move a substantially greater distance than the given distance.

Preferred embodiments of this aspect of the invention include one or more of the following features.

The cable is attached to the body at an electrical terminal capable of transmitting an electrical cauterizing current. Preferably the cable is capable of transmitting cauterizing electrical current and the snare loop is attached to the cable so that cauterizing electrical current may be transmitted from the cable to the snare.

The cable is substantially laterally confined throughout its entire length to enable transmission of axial thrust on the snare loop.

The pulley surface is defined by a rigid formation rigidly joined to the actuating member about which relative sliding motion of the cable portion occurs during actuation and which defines a track with a diameter small enough to support the cable against columnar buckling.

The pulley surface is rotatably mounted on the actuating member, the cable is trained about the pulley surface such that movement of the cable causes a corresponding rotation of the pulley, and the pulley surface defines a track with a diameter small enough to support the cable against columnar buckling.

The cable is partially contained by a sheath.

In yet another aspect, the invention comprises a medical snare device having a body, a thumb loop integral with the body, an actuating member mounted to move relative to the body, a sheath, a snare loop at a distal portion of the device and capable of being fully retracted within the sheath, an electrical terminal, at least one cannula telescopically engaged in the actuating member and at least one cannula telescopically engaged in the body, and a cable capable of transmitting actuating force between the actuating member and the snare loop. The cable is attached on one end to the body at the electrical terminal and is associated in a driving relationship on the opposite end with the snare loop. The cable is supported against columnar buckling by the cannulae. According to the invention, the actuating member includes at least one finger loop and a pulley surface bodily movable therewith, the cable is trained about the pulley surface such that movement of the actuating member a given distance, relative to the body, causes the snare loop to move a substantially greater distance than the given distance.

DESCRIPTION OF PREFERRED EMBODIMENTS

Figure 1:
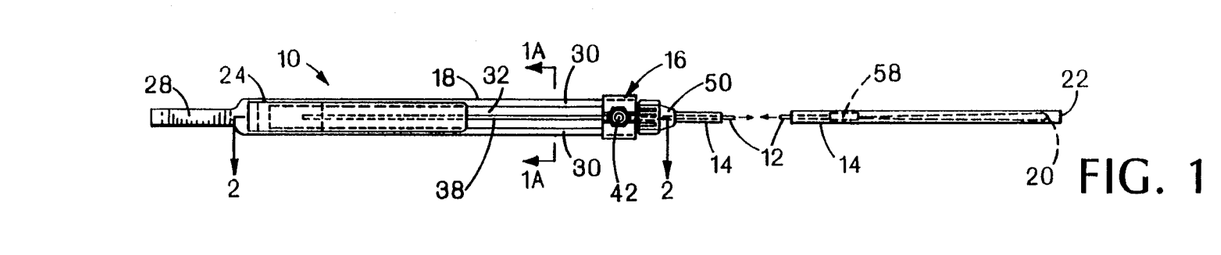
FIG. 1 is a top view, partially broken away, of a preferred embodiment of the invention.
Figure 1A:
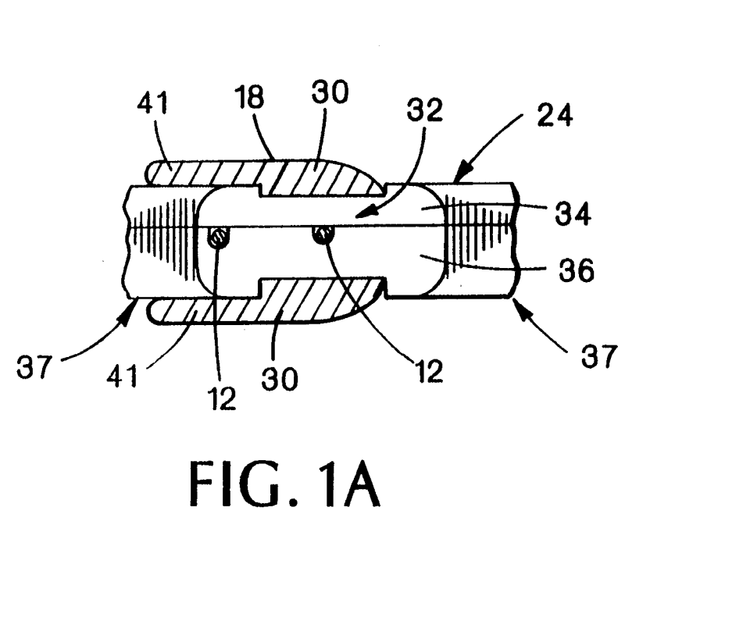
FIG. 1A is a transverse cross-sectional view on an enlarged scale taken on line 1a–1a of FIG. 1.
Figure 2:
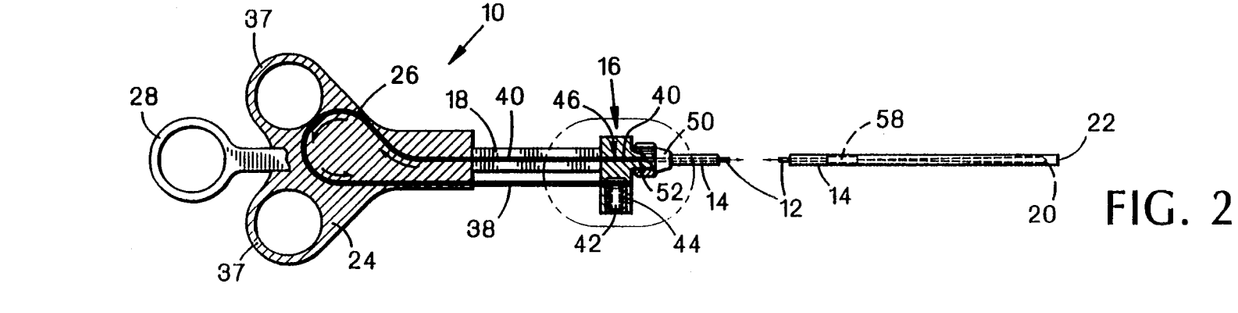
FIG. 2 is a longitudinal, cross-sectional view, partially broken away, of the preferred embodiment of FIG. taken on line 2—2 of FIG. 1.
Figure 2A:
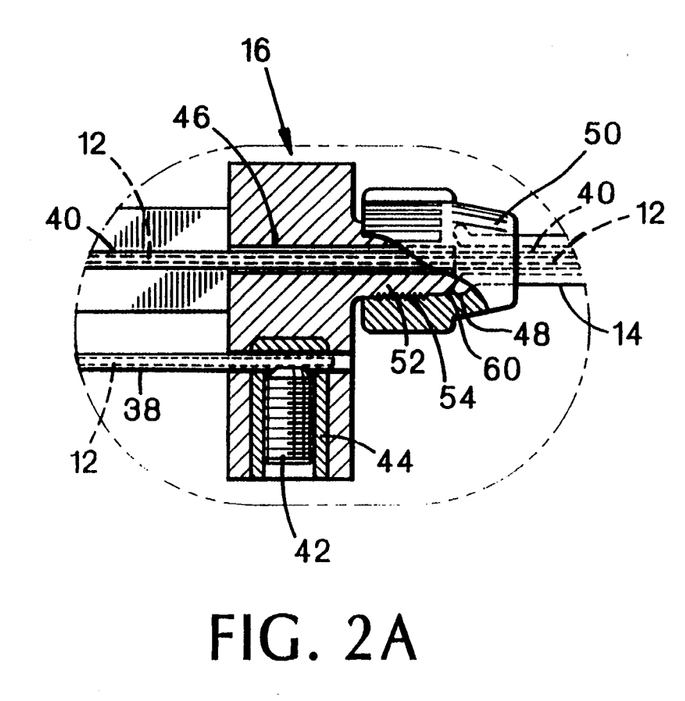
FIG. 2A is a cross-sectional view on an enlarged scale of the portion of the device in FIG. 2 encircled by the chained lines.
Figure 3:
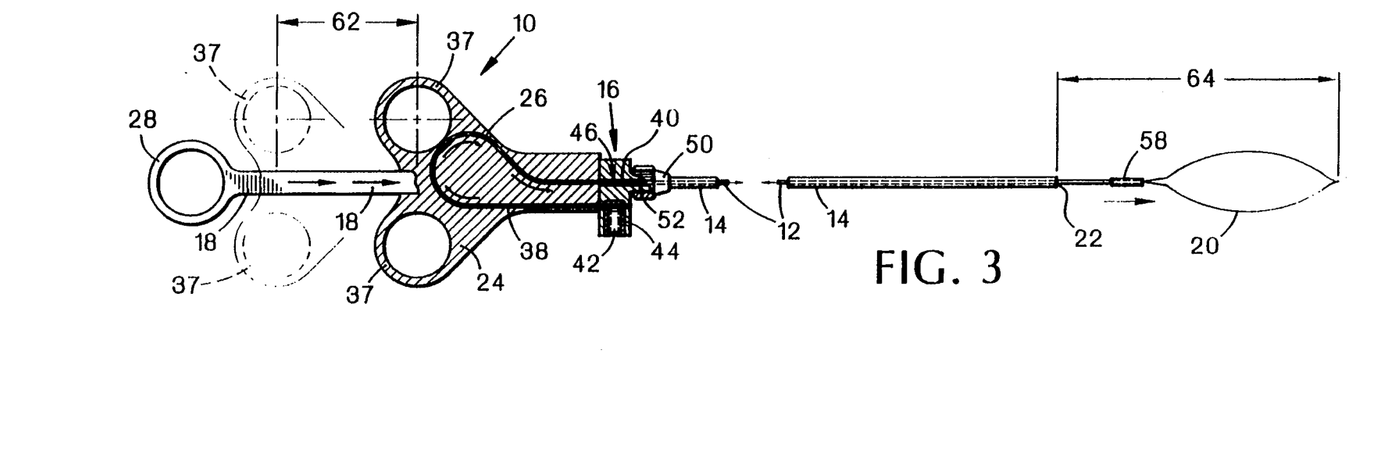
FIG. 3 is a view similar to FIG. 2 showing the positions of the handle of the device during actuation and depicting the snare in solid lines in its extended position.
Figure 4:
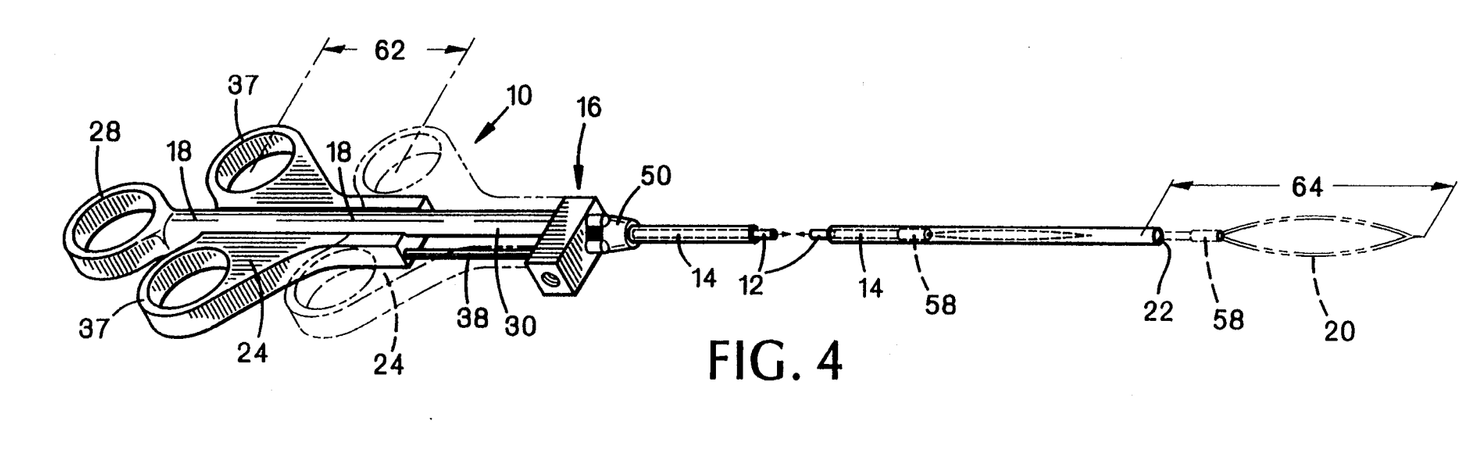
FIG. 4 is a perspective view of the embodiment of FIGS. 1–3 illustrating the two positions of the handle as indicated in FIG. 3, with the handle in solid lines in the retracted position.

Referring now generally to FIGS. 1–3, small handle 10 advances and withdraws cable 12 within sheath 14. The proximal end of cable 12 is fixed to nose 16 of handle body 18. At the distal end of cable 12 is snare loop 20, which can be used to excise a polyp (not shown) by advancing snare loop 20 beyond tip 22 of sheath 14, looping snare loop 20 around the polyp, and then retracting snare loop 20 into sheath 14 such that snare loop 20 is entirely retracted through sheath tip 22.

Handle body 18, preferably, is a single injection molded component composed of nylon or other resilient material having legs 30 which define channel 32. A thumb ring 28 is located at one end of handle body 18 to enable an operator to control it, and, if desired, thumb ring 18 may be rotatable.

Referring more specifically to FIG. 1a, actuating member 24 is slidably disposed on handle body 18 between legs 30 in channel 32. Actuating member 24 preferably is made of nylon, DELRYN, or any suitable polymeric injection molded material. Actuating member 24 may be manufactured as a clam shell with top half 34 and bottom half 36 separately injection molded and later joined by melting, snap fitting, through the application of an adhesive such as cyanoacrylate, or clamped together by legs 30 of handle body 18. As shown in FIGS. 1–3, actuating member 24 preferably has two finger loops disposed on opposite sides of handle body 18 for engagement by fingers of an operator.

Pulley surface 26 is disposed on actuating member 24 and may be rotary or stationary. In a preferred embodiment pulley surface 26 defines a rigid, semi-circular track integral with actuating member 24 and has a cross section only slightly larger than cable 12 to prevent cable 12 from buckling under compressive force.

Figure 6:
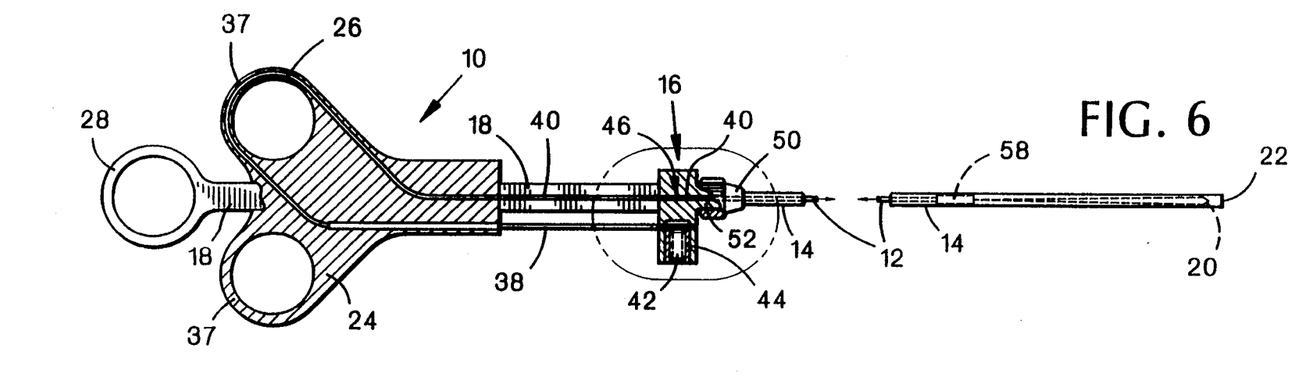
FIGS. 6 and 7 are views similar to FIG. 2 showing alternate embodiments of the invention.

Pulley surface 26 may be located as shown in FIGS. 2 and 3 or may be located at another position on actuating member 24, such as the embodiment shown in FIG. 6, where pulley surface 26 corresponds with finger hole 37.

Figures 7, 7A:
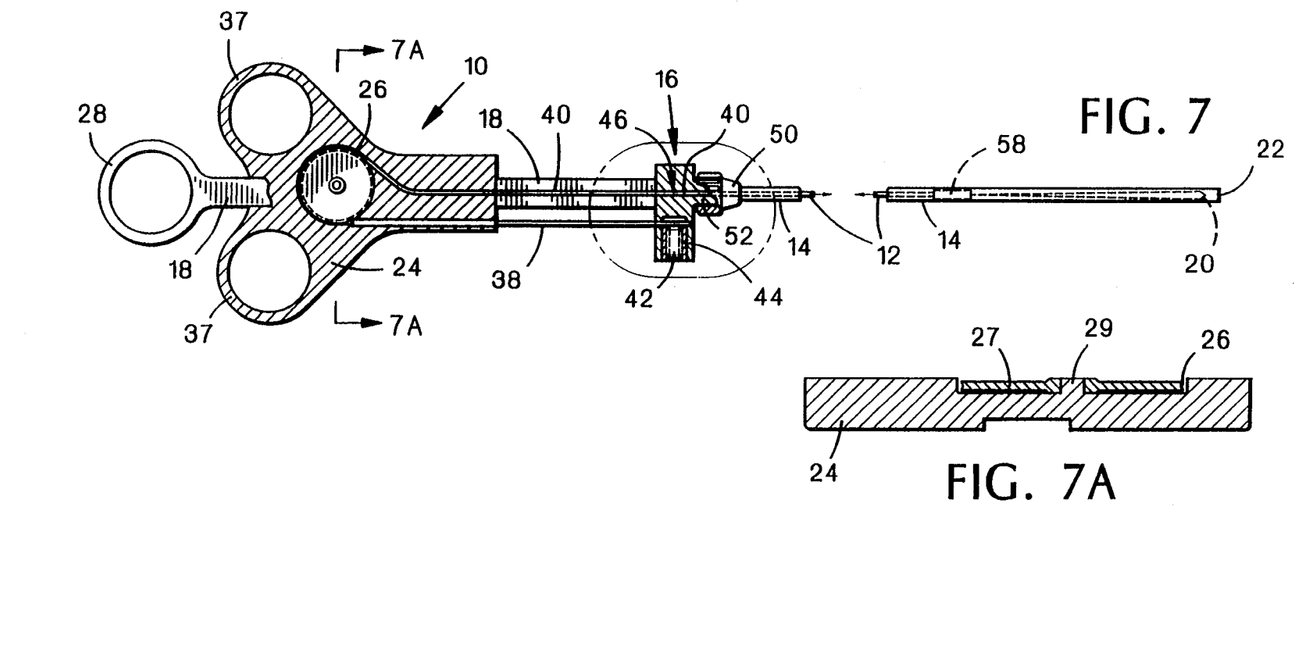
FIG. 7a is a longitudinal, cross-sectional view, of the embodiment of FIG. 7, taken on line 7a–7a of FIG. 7.
Figure 8:
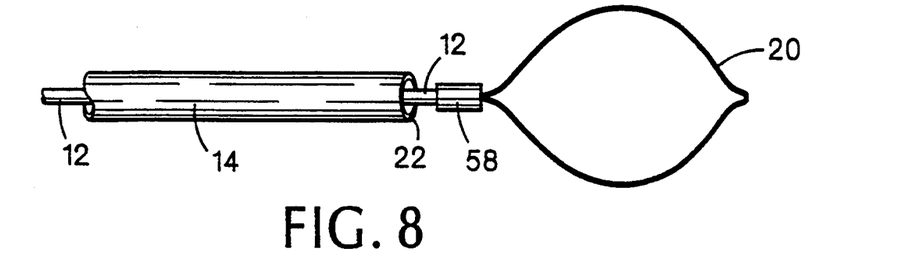
FIGS. 8–18 are perspective views of alternate working elements which may be used in conjunction with the invention.
Figure 9:
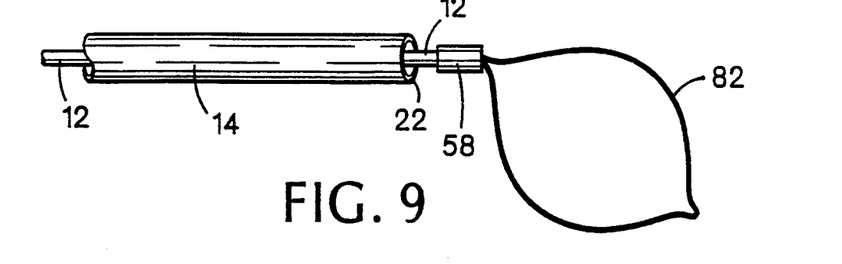
Figure 10:
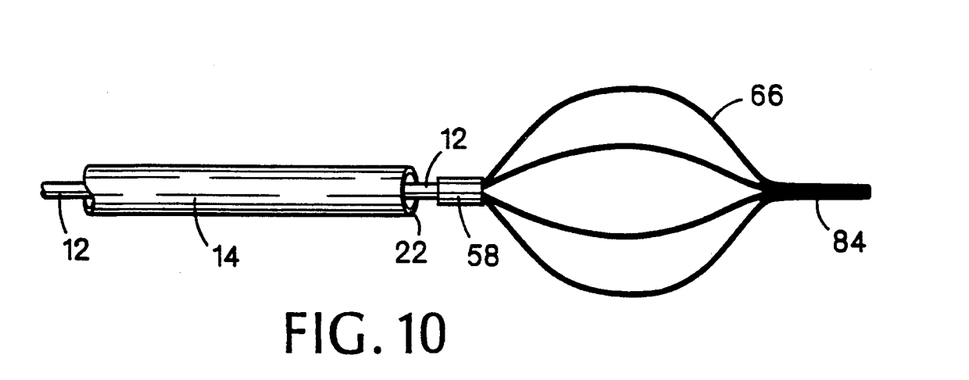

Pulley surface 26 may also be rotatable as shown in FIGS. 7 and 7a. In this embodiment, pulley 27 is rotatably mounted on axle 29. Pulley surface 26 may be flat or indented to accommodate cable 12.

A biocompatible silicon type lubricant may be used to reduce friction on pulley surface 26 in embodiments of the invention employing both fixed and rotatable pulley surfaces.

The pulley advantage of pulley surface 26, which is in direct contact with cable 12, allows the operator to achieve the desired two to one activation ratio, while the absence of intervening parts provides the tactile feeling previously only available in handles with a one to one activation ratio.

Referring now to FIG. 2A, cable 12 passes through nose 16 of handle body 18 around pulley surface 26 on actuating member 24, and back to nose 16 where the end of cable 12 is fixed to nose 16. Cable 12 is confined throughout its entire pathway within medical device 10 to prevent columnar buckling. Preferably, cannulae 38 and 40 are used to confine cable 12 between nose 16 and actuating member 24. Cable 12 is connected, by soldering or any other method, to one end of cannula 38. This end is attached body 18 by set screw 42 disposed in can 44 on nose 16. The other end of cannula 38 is telescopically disposed within actuating member 24. Similarly, cannula 40 has one end attached to actuating member 24 and the other end telescopically disposed within aperture 46 in nose 16.

Figure 5:
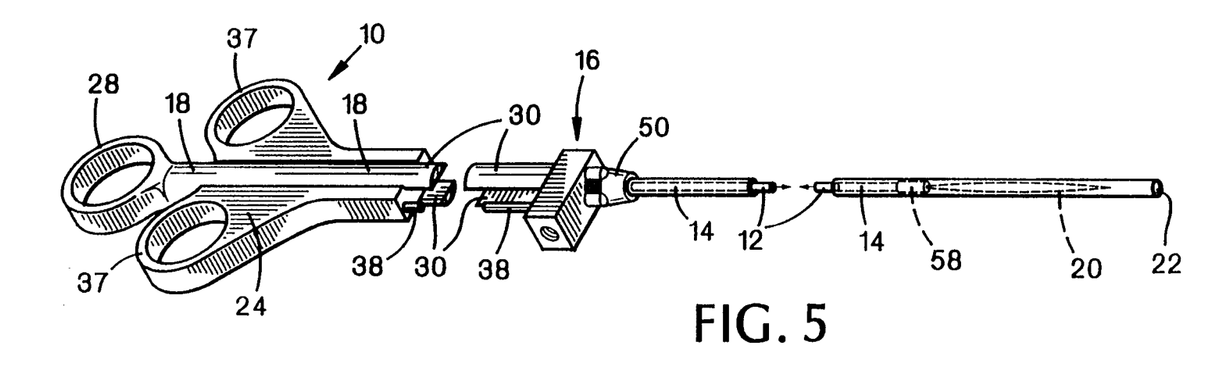
FIG. 5 is a view similar to FIG. 4 illustrating the position achieved by the snare after actuation in which the snare has retracted into the tube of the device.

Referring now to FIG. 5, actuation of the snare handle causes cable 12 to move about pulley surface 26, through cannula 40 and out nose 16. Due to the pulley advantage of pulley surface 26, movement of actuating member 24 a given distance 62 results in translation of cable 12 twice the given distance 64. Similarly, when actuating member 24 is retracted, cable 12 retracts twice as far as the movement of actuating member 24 due to the pulley advantage of pulley surface 26. This two-fold increase in the cable stroke relative to movement of actuating member 24 permits a nurse with small hands to operate the snare handle with one hand.

Cable 12 is preferably a stainless steel braided cable that is quite stiff and not prone to buckle under compression. Cable 12 could, however, be any other electrical conductive, such as single strand wire, which is capable of withstanding both tensile and compressive forces, and may have rigid portions. The cable currently contemplated to be used by the invention has a diameter from 10 to 60 thousandths of an inch and more preferably from 30 to 40 thousandths, although other cable diameters may be acceptable.

Cannulae 38 and 40 are preferably stainless steel tubes which confine cable 12 and allow about five thousandths of an inch clearance between the inside wall of the tube and the cable. The cannula wall is preferably about two thousandths of an inch thick. The exterior of cannula 38 and 40 may be coated with an insulator such as nylon to prevent a person operating the medical device from being shocked. Alternatively, as shown in FIG. 1A, guard 41 (a part of body 18 which extends outward from legs 30 to cover cannula 38) may be included for this same purpose.

Referring now to FIG. 2A, set screw 42 attaches cannula 38 to body 18 such that an electrical connection forms. If a connector is attached to the set screw, an electrical current, such as r-f, may be applied to cable 12, thereby allowing for electrical cauterization of a polyp by snare loop 20.

Sheath 14 has flared end 48 which is attached by compression cap 50 to side extension 52 of nose 16. Side extension 52 carries a plurality of threads 54 on an outer surface and has beveled front 60 which mates with flared end 48. Compression cap 50 is threaded onto side extension 52 and traps flared end 48 against beveled front 60.

The inside of sheath 14 aligns with aperture 46 in nose 16 and is large enough that cannula 40 may be telescopically disposed in it, but must also be small enough to prevent cable 12 from buckling upon application of compressive force. Sheath 14 is preferably made of teflon or another lubricous flexible material which does not conduct electricity. Tip 22 of sheath 14 may be cut on any desired angle.

Referring now to FIG. 3, snare loop 20 is preferably attached to the distal end of cable 12 by crimp connector 58, however, another means of connection, such as soldering or brazing, may be used. It is desirable that this connection be capable of conducting electricity from cable 12 to snare loop 20.

Snare loop 20 is preferably stainless steel braided wire of a lesser diameter than cable 12, usually from 20 to 40 thousandths of an inch in diameter. Snare loop 20 should be flexible to withdraw into the end of sheath 14, and should be resilient and retain its shape when extended.

Figure 11:
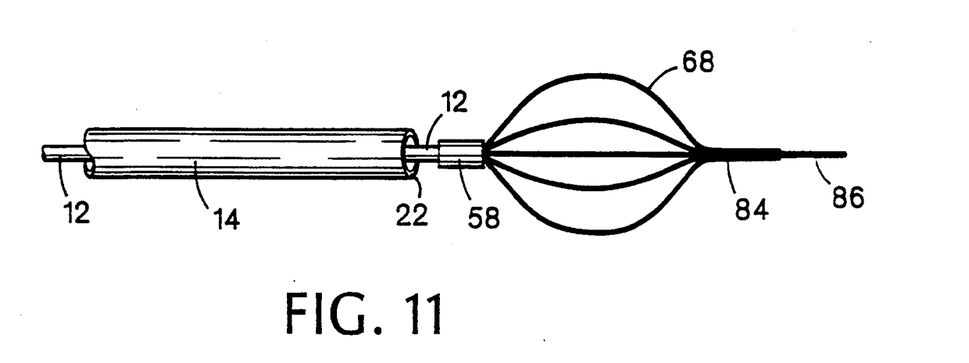
Figure 12:
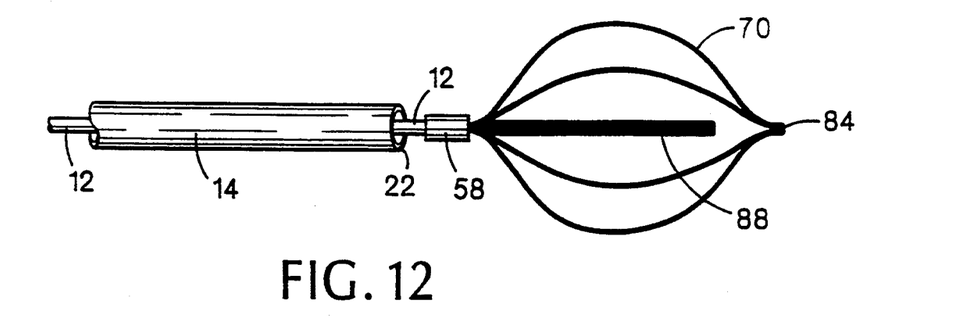
Figure 13:
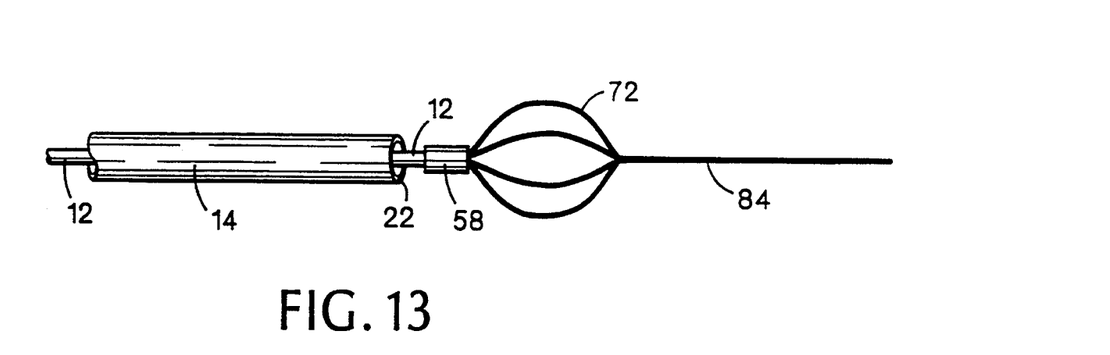
Figure 14:
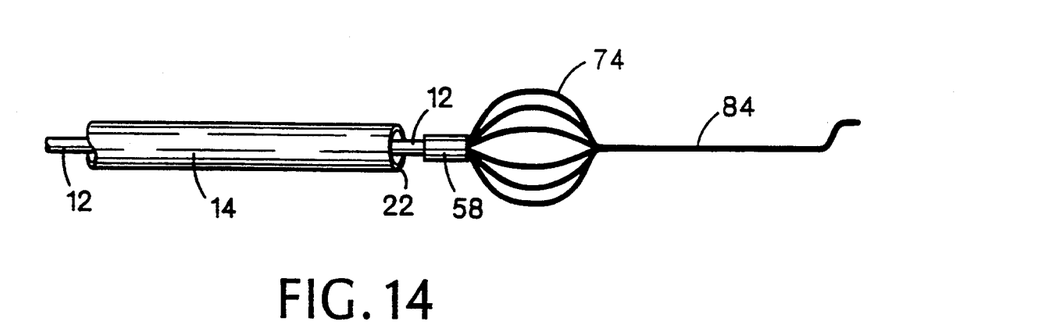
Figure 15:
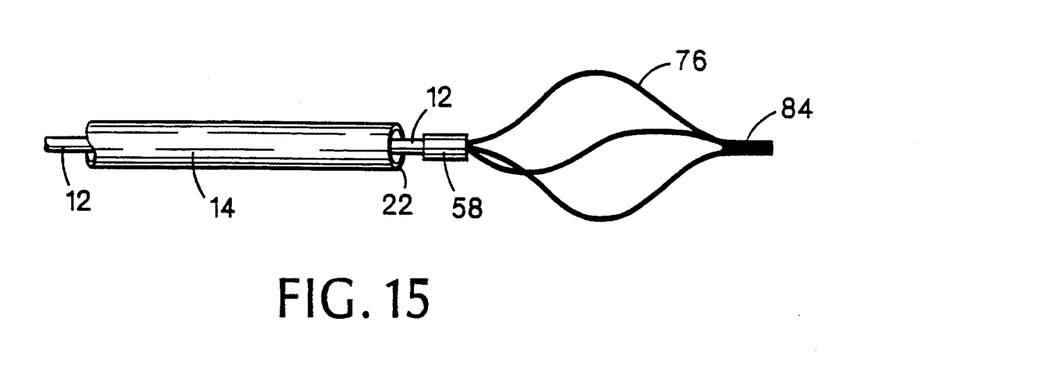
Figure 16:
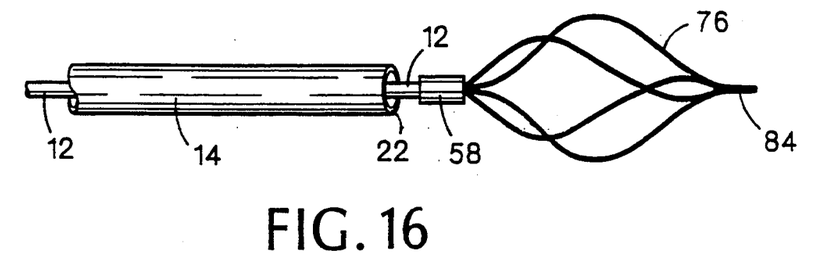
Figure 17:
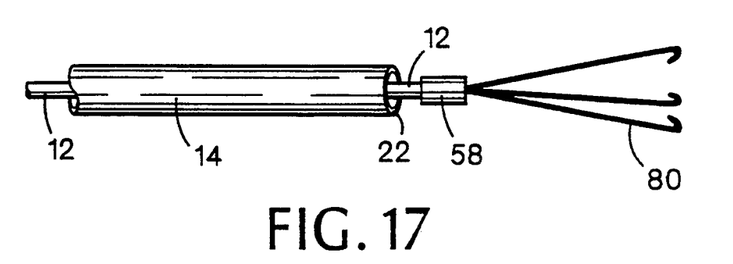
Figure 18:
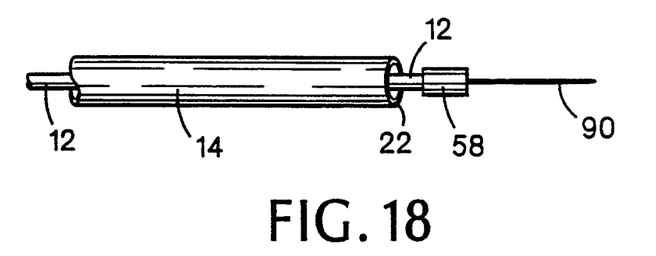

As shown in FIGS. 8–18, other types of working elements such as baskets 66–78, grasping forceps 80, right angle snare loop 82, or point type cauterization device 90 may be substituted for snare loop 20. Baskets 66–78 may have tips 84 of any desired length or shape, and the number of wires may vary, although usually four or six wires are used. As shown in FIG. 11, basket 68 may be designed to slide upon guide wire 86, or, as shown in FIG. 12, basket 68 may be designed to accommodate pulsed-dye laser fiber-optic probe 88. Grasping forceps 80 may have three prongs as shown in FIG. 17 or any other desired number of prongs. Point type cauterization device 90 may be any type of needle, wire or electrode.

Figure 19:
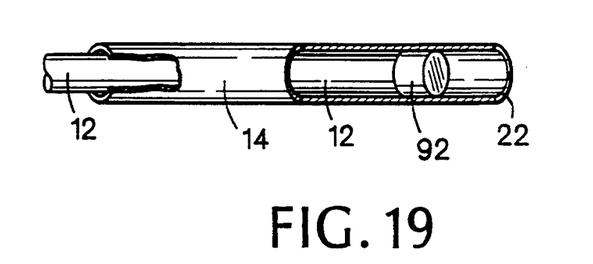
FIG. 19 is a longitudinal, cross-sectional view, partially broken away, of a working element of an embodiment of the invention as used in a syringe.

The snare handle described above may also be useful in other areas of medicine, such as laparoscopic surgery, or as a syringe handle. It occasionally is necessary to pickup or deliver very small amounts of drugs such as Tpa. As shown in FIG. 19, when the medical device of the invention is used as a syringe, sheath 14 is reduced in size so that the inside diameter of sheath 14 is substantially identical to the diameter of cable 12. Preferably, the clearance between sheath 14 and cable 12 would be one to two thousandths of an inch. The working element in this embodiment of the invention is a device such as plug 92, which is disposed on the end of cable 12 such that a seal is formed between plug 92 and the inside of sheath 14. When the cable is withdrawn, this seal causes a suction which draws fluid into the end of sheath 12. Preferably, the length of cable 12 is adjusted so that plug 92 remains within sheath 14 regardless of the position of actuating member 24 on body 18. The length of cable 12 must also be adjusted so that plug 92 will extend completely to tip 22 of sheath 14. Plug 92 may be any type of material, such as rubber, which will cause a seal to form.

Figure 20:
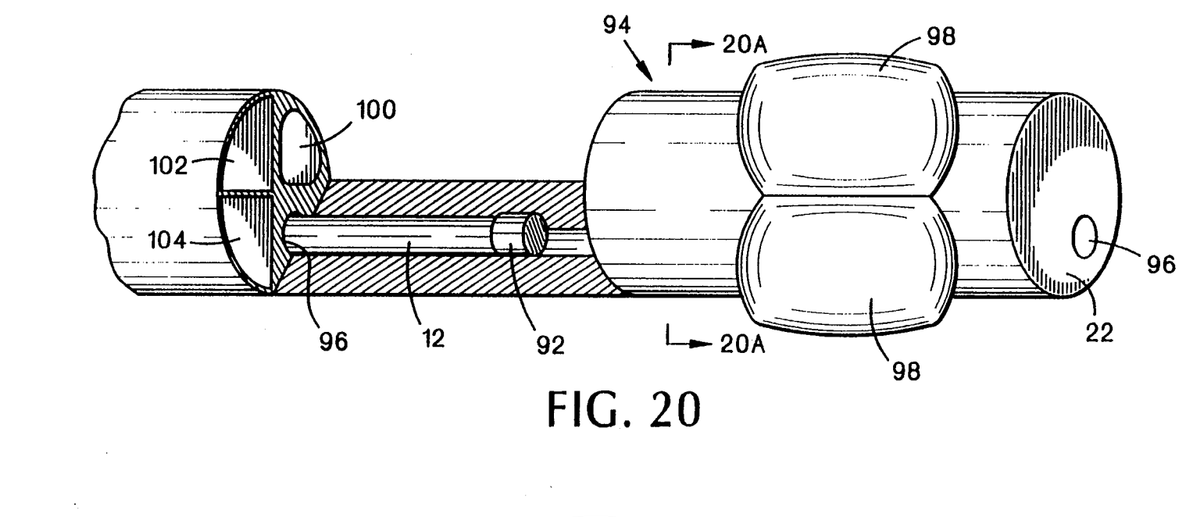
FIG. 20 is a perspective view, partially broken away, of an embodiment of the invention as used with a balloon catheter.
Figure 20A:
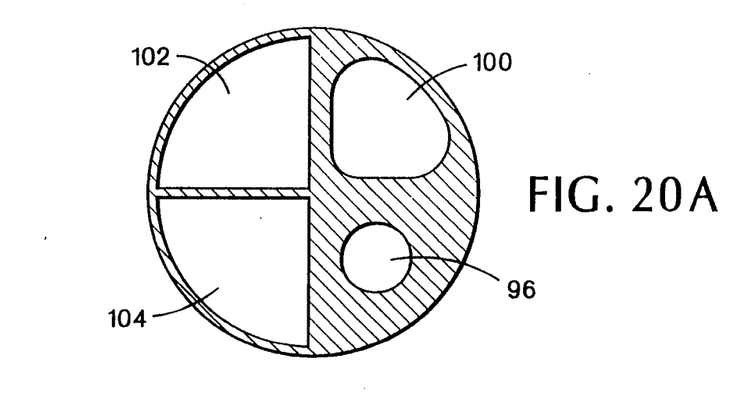
FIG. 20a is a cross section taken on line 20a–20a of FIG. 20.

As shown in FIGS. 20 and 20a, the medical device of the invention could be used in conjunction with a single balloon or multi-balloon catheter 94 by inserting cable 12 and associated working element, preferably plug 92, through lumen 96. Balloons 98 are inflated by the introduction of fluid through lumens 100, 102 and 104 which may be of any desired shape. Lumens 100, 102, and 104 preferably run the length of balloon catheter 94, but do not intersect catheter end 22.

What is claimed is:

1. A medical device comprising a body, an actuating member mounted to said body in a manner permitting relative movement therebetween, a working element remote from said body, and an elongated force-transmitting member extending between said actuating member and said working element and capable of transmitting bi-directional actuating force between said actuating member and said working element, said actuating member including a pulley surface bodily movable therewith, said force-transmitting member including a flexible cable portion trained about said pulley surface such that movement of said actuating member in either direction a given distance, relative to said body, causes said working element to move a substantially greater distance than said given distance.

2. The medical device of claim 1 wherein said pulley surface is defined by a rigid formation that is rigidly joined to said actuating member, and said cable portion being slidable relative to said pulley surface during the movement of said actuating member.

3. The medical device of claim 1 wherein the flexible cable portion of said force-transmitting member is substantially confined throughout its length enabling transmission of axial thrust on said working element.

4. The medical device of claim 1 wherein said actuating member is mounted to translate relative to said body, thereby translating said pulley surface relative to said body.

5. The medical device of claim 1 wherein said body includes a rigid proximal portion adjacent to said actuating member and an elongated flexible distal portion through which said force-transmitting member extends.

6. The medical device of claim 5 wherein said elongated flexible distal portion comprises a medical catheter.

7. The medical device of claim 1 wherein said force-transmitting member comprises a flexible metal cable extending from a point of attachment on said body to said working element.

8. The medical device of claim 7 wherein said cable is of a form capable of transmitting both tensile and compressive forces from the actuating member to said working element.

9. The medical device of claim 1 wherein said actuating member further comprises at least one loop engageable by a finger of an operator.

10. The medical device of claim 9 wherein said body terminates in a relatively stationary thumb loop centrally located on said body, and said actuating member defines two finger loops disposed on opposite sides of said thumb loop.

11. The medical device of claim 1 wherein said actuating member includes a rigid guide tube slidably engaged with said body, said force-transmitting member extending through said guide tube in a sliding relationship.

12. The medical device of claim 1 wherein said working element is a snare.

13. The medical device of claim 1 wherein said working element is an angled snare loop.

14. The medical device of claim 1 wherein said working element is a grasper.

15. The medical device of claim 1 wherein said working element is a basket.

16. A medical snare device comprising a body, an actuating member mounted to said body in a manner permitting movement therebetween, a snare remote from said body, and a cable extending between said actuating member and said snare and capable of transmitting bi-directional actuating force between said actuating member and said snare, said actuating member including a pulley surface bodily movable therewith, said cable being trained about said pulley surface such that movement of said actuating member in either direction a given distance, relative to said body, causes said snare to move a substantially greater distance than said given distance.

17. The medical snare device of claim 12 wherein said body further comprises an electrical terminal to which said cable is attached, said electrical terminal being capable of transmitting an electrical cauterizing current.

18. The medical snare device of claim 17 wherein said cable is capable of transmitting the electrical cauterizing current.

19. The medical snare device of claim 18 wherein said cable is attached to said snare in a manner enabling said cable to transmit the electrical cauterizing current to said snare.

20. The medical snare device of claim 16 wherein said cable is substantially laterally confined throughout its entire length enabling transmission of axial thrust on said snare.

21. The medical snare device of claim 16 wherein said pulley surface is defined by a rigid formation that is rigidly joined to said actuating member and defines a track with a diameter small enough to support said cable against columnar buckling, and said cable being slidable relative to said pulley surface during the movement of said actuating member.

22. The medical snare device of claim 12 wherein said pulley surface is defined by a member rotatably mounted on said actuating member, said cable being trained about said pulley surface such that movement of said cable causes a corresponding rotation of said pulley, said pulley surface defining a track with a diameter small enough to support said cable against columnar buckling.

23. The medical snare device of claim 12 wherein said cable is partially contained by a sheath.

24. A medical snare device comprising a body, a thumb loop integral with said body, an actuating member mounted to said body in a manner permitting relative movement therebetween, a sheath extending distally from said body, an electrical terminal integral with said body, a snare loop remote from said device, and a cable extending between said body at said electrical terminal and said snare loop, said cable being capable of transmitting actuating force between said actuating member and said snare loop, said snare loop capable of being fully retracted within said sheath,
  at least one cannula telescopically engaged in said actuating member and at least one cannula telescopically engaged in said body, said cable supported against columnar buckling by said cannulae,
  said actuating member including at least one finger loop and a pulley surface bodily movable with said actuating member, said cable being trained about said pulley surface such that movement of said actuating member a given distance, relative to said body, causes said snare loop to move a substantially greater distance than said given distance.

* * * * *

UNITED STATES PATENT AND TRADEMARK OFFICE
CERTIFICATE OF CORRECTION

PATENT NO. : 5,376,094

DATED : December 27, 1994

INVENTOR(S) : Craig R. Kline

Page 1 of 2

It is certified that error appears in the above-indentified patent and that said Letters Patent is hereby corrected as shown below:

Col. 1, after the title insert --This invention relates to polypectomy snares and other actuated medical devices.--

Col. 2, line 8, after "features" insert a period.

Col. 3, line 42, after "FIG." insert --1--.

Col. 4, line 6, "small" should be --snare--.

Col. 4, line 68, after "attached" insert --to--.

Col. 7, claim 12, line 40, after "snare" insert --loop--.

UNITED STATES PATENT AND TRADEMARK OFFICE
CERTIFICATE OF CORRECTION

PATENT NO. : 5,376,094
DATED : December 27, 1994
INVENTOR(S) : Craig R. Kline

It is certified that error appears in the above-indentified patent and that said Letters Patent is hereby corrected as shown below:

Col. 8, claim 17, line 3, "12" should be --16--.

Col. 8, claim 22, line 25, "12" should be --16--.

Col. 8, claim 22, line 29, after "of said" insert --surface--.

Col. 8, claim 23, line 33, "12" should be --16--.

Col. 8, claim 23, line 34, "by" should be --within--.

Col. 8, claim 23, line 34, after "sheath" insert --attached to said body within--.

Signed and Sealed this

Twenty-third Day of July, 1996

Attest:

Attesting Officer

BRUCE LEHMAN
Commissioner of Patents and Trademarks